(12) United States Patent
Russo et al.

(10) Patent No.: US 9,039,752 B2
(45) Date of Patent: May 26, 2015

(54) DEVICE AND METHOD FOR DELIVERING A VASCULAR DEVICE

(75) Inventors: Patrick Russo, Vadnais Heights, MN (US); Mark Krans, St. Louis Park, MN (US); Matthew C. Heidner, Maple Grove, MN (US)

(73) Assignee: AGA Medical Corporation, Plymouth, MN (US)

( * ) Notice: Subject to any disclaimer, the term of this patent is extended or adjusted under 35 U.S.C. 154(b) by 225 days.

(21) Appl. No.: 13/236,803

(22) Filed: Sep. 20, 2011

(65) Prior Publication Data

US 2013/0073024 A1 Mar. 21, 2013

(51) Int. Cl.
*A61F 2/966* (2013.01)
*A61F 2/95* (2013.01)

(52) U.S. Cl.
CPC ......... *A61F 2/966* (2013.01); *A61F 2002/9522* (2013.01); *A61F 2002/9534* (2013.01); *A61F 2002/9665* (2013.01)

(58) Field of Classification Search
USPC ................. 606/194, 195, 198; 623/1.11–1.16
See application file for complete search history.

(56) References Cited

U.S. PATENT DOCUMENTS

| | | | |
|---|---|---|---|
| 4,655,771 A | 4/1987 | Wallsten | |
| 4,728,328 A | 3/1988 | Hughes et al. | |
| 4,954,126 A | 9/1990 | Wallsten | |
| 5,064,435 A | 11/1991 | Porter | |
| 5,522,881 A | 6/1996 | Lentz | |
| 5,628,788 A | 5/1997 | Pinchuk | |
| 5,645,559 A | 7/1997 | Hachtman et al. | |
| 5,646,559 A | 7/1997 | Higurashi | |
| 5,667,523 A | 9/1997 | Bynon et al. | |
| 5,741,325 A | 4/1998 | Chaikof et al. | |
| 5,758,562 A | 6/1998 | Thompson | |
| 5,800,508 A | 9/1998 | Goicoechea et al. | |
| 5,824,042 A | 10/1998 | Lombardi et al. | |

(Continued)

FOREIGN PATENT DOCUMENTS

| EP | 2143404 | 1/2010 |
|---|---|---|
| WO | WO-95/32757 | 12/1995 |

(Continued)

OTHER PUBLICATIONS

International Search Report and Written Opinion of the Search Authority for Application No. PCT/US2012055721; dated Nov. 27, 2012.

(Continued)

*Primary Examiner* — Tuan V Nguyen
(74) *Attorney, Agent, or Firm* — Armstrong Teasdale LLP

(57) ABSTRACT

A device and method for delivering a vascular device to a target site is provided that maintains a proximal portion of the vascular device within a tubular sleeve by positioning a stop of an inner member at a distal opening of the tubular sleeve to block the opening. Once the stop has been moved distally via movement of the inner member to clear the opening, a band of increased thickness on the inner member can urge the proximal portion of the vascular device out of the tubular sleeve to deploy the vascular device. The vascular device may be recaptured within a delivery sheath prior to the full deployment of the proximal portion of the vascular device from the tubular sleeve by re-positioning the stop at the distal opening to hold the vascular device within the tubular sleeve as the delivery device is retracted with respect to the delivery sheath.

14 Claims, 11 Drawing Sheets

(56) References Cited

U.S. PATENT DOCUMENTS

| | | | |
|---|---|---|---|
| 5,824,055 | A | 10/1998 | Spiridigliozzi et al. |
| 5,860,998 | A | 1/1999 | Robinson et al. |
| 5,916,264 | A | 6/1999 | Von Oepen et al. |
| 5,957,974 | A | 9/1999 | Thompson et al. |
| 6,096,052 | A | 8/2000 | Callister et al. |
| 6,110,198 | A | 8/2000 | Fogarty et al. |
| 6,123,715 | A | 9/2000 | Amplatz |
| 6,156,064 | A | 12/2000 | Chouinard |
| 6,221,099 | B1 | 4/2001 | Andersen |
| 6,264,689 | B1 | 7/2001 | Colgan et al. |
| 6,299,636 | B1 | 10/2001 | Schmitt et al. |
| 6,500,203 | B1 | 12/2002 | Thompson et al. |
| 6,613,078 | B1 | 9/2003 | Barone |
| 6,709,451 | B1 | 3/2004 | Noble et al. |
| 6,932,837 | B2 | 8/2005 | Amplatz et al. |
| 6,978,643 | B2 | 12/2005 | Akers et al. |
| 7,175,655 | B1 * | 2/2007 | Molaei ............ 623/1.18 |
| 7,473,271 | B2 * | 1/2009 | Gunderson ............ 623/1.12 |
| 7,942,924 | B1 | 5/2011 | Perez et al. |
| 8,114,147 | B2 | 2/2012 | Wood et al. |
| 8,163,004 | B2 | 4/2012 | Amplatz et al. |
| 8,182,522 | B2 * | 5/2012 | Sarac et al. ............ 623/1.11 |
| 2003/0135265 | A1 | 7/2003 | Stinson |
| 2006/0229697 | A1 * | 10/2006 | Gerdts et al. ............ 623/1.11 |
| 2006/0253184 | A1 | 11/2006 | Amplatz |
| 2007/0106211 | A1 | 5/2007 | Provost-Tine et al. |
| 2007/0118207 | A1 | 5/2007 | Amplatz et al. |
| 2007/0168018 | A1 | 7/2007 | Amplatz et al. |
| 2007/0168019 | A1 | 7/2007 | Amplatz et al. |
| 2007/0265656 | A1 | 11/2007 | Amplatz et al. |
| 2008/0281398 | A1 | 11/2008 | Koss et al. |
| 2008/0288043 | A1 | 11/2008 | Kaufmann et al. |
| 2009/0036966 | A1 * | 2/2009 | O'Connor et al. ............ 623/1.11 |
| 2009/0112251 | A1 | 4/2009 | Qian et al. |
| 2009/0171427 | A1 | 7/2009 | Melsheimer et al. |
| 2009/0210047 | A1 | 8/2009 | Amplatz et al. |
| 2009/0210048 | A1 | 8/2009 | Amplatz et al. |
| 2009/0312834 | A1 | 12/2009 | Wood et al. |
| 2010/0023046 | A1 | 1/2010 | Heidner et al. |
| 2010/0023048 | A1 | 1/2010 | Mach |
| 2010/0106235 | A1 | 4/2010 | Kariniemi et al. |
| 2012/0150277 | A1 | 6/2012 | Wood et al. |

FOREIGN PATENT DOCUMENTS

| | | |
|---|---|---|
| WO | WO-2006/014233 | 2/2006 |
| WO | WO-2011/094527 | 8/2011 |

OTHER PUBLICATIONS

International Search Report and Written Opinion for Application No. PCT/US2012/055718 dated Mar. 8, 2013.

International Search Report for Application No. PCT/US2012/055718; dated Nov. 23, 2012.

* cited by examiner

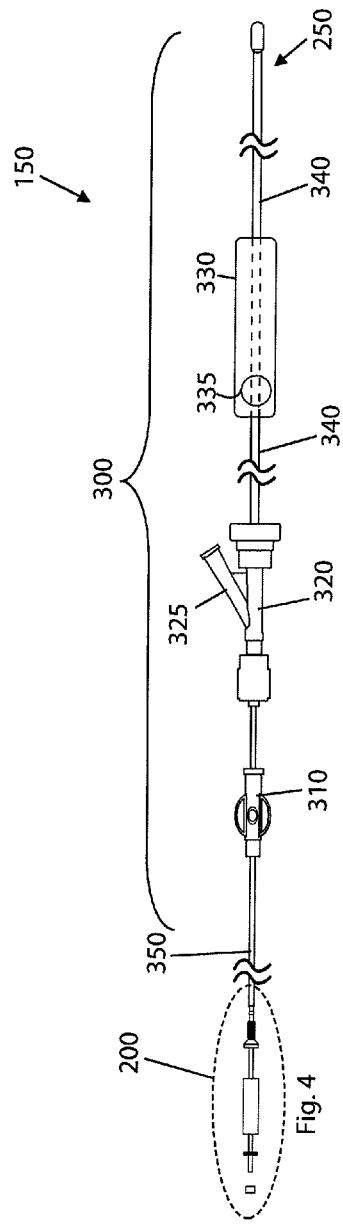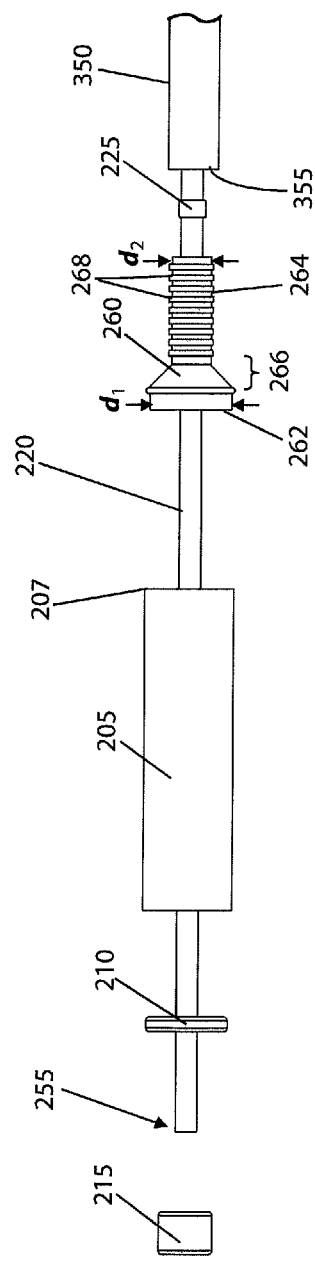
FIG. 3
FIG. 4

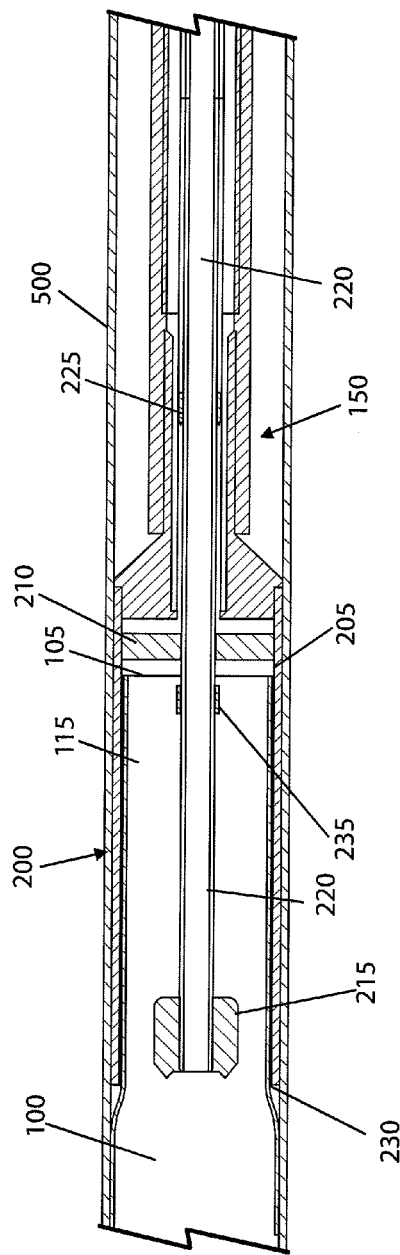
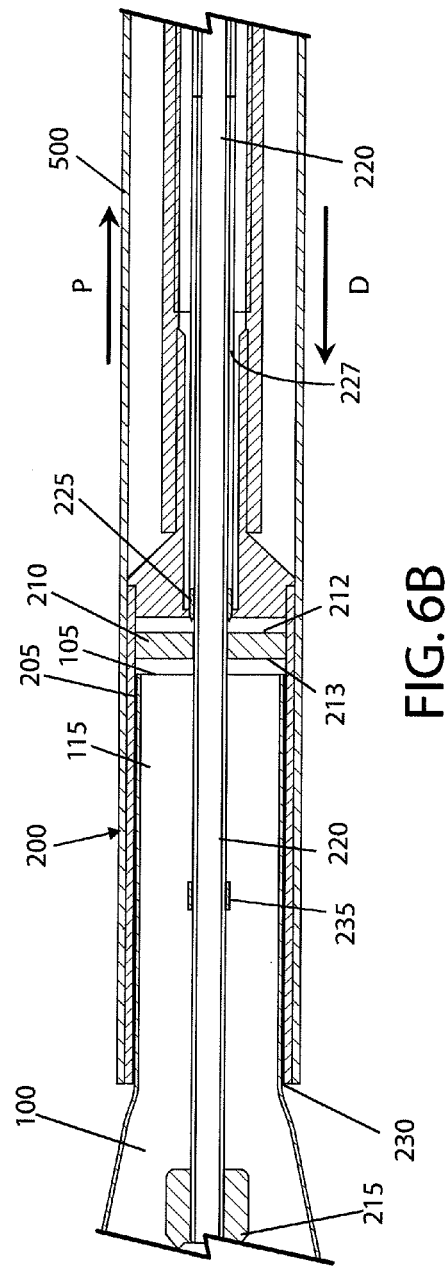
FIG. 6A
FIG. 6B

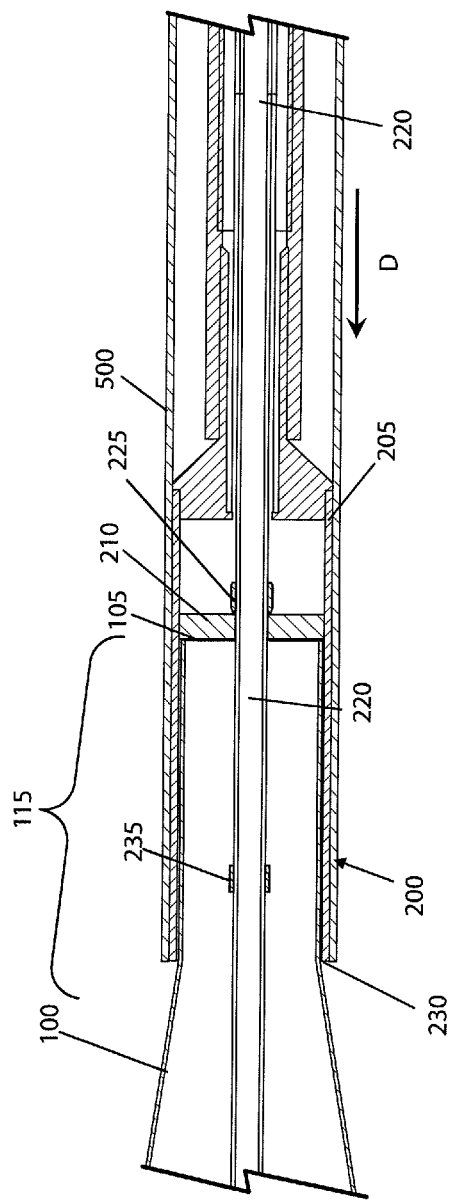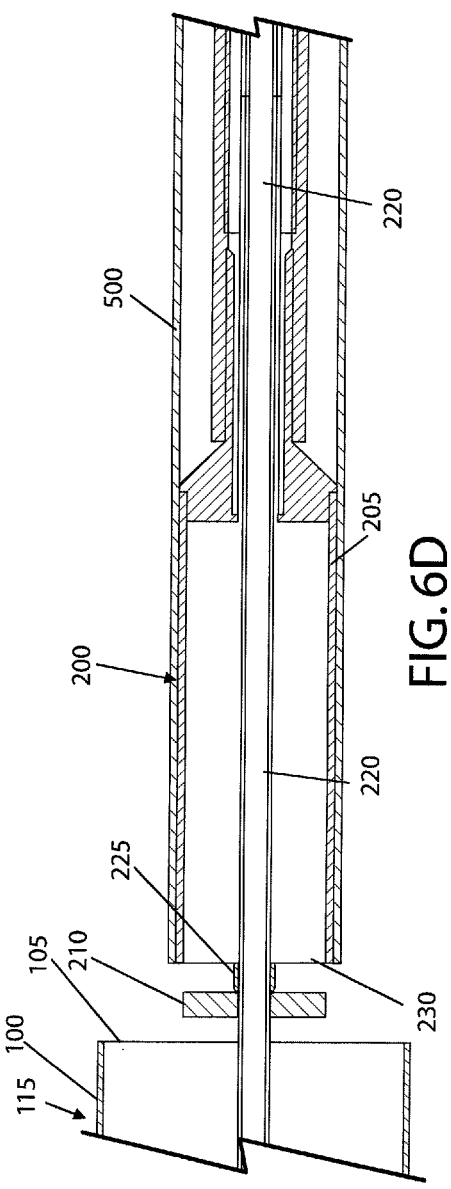

DEVICE AND METHOD FOR DELIVERING A VASCULAR DEVICE

BACKGROUND

I. Field of the Invention

Embodiments of the present invention relate generally to delivery devices for positioning and deploying vascular devices within a body lumen for treating certain medical conditions. In particular, embodiments are directed to devices and methods for delivering and deploying vascular devices including stents, grafts, and stent-grafts having a low profile in the vasculature of a patient, such as the vessels of the thoracic area.

II. Description of the Related Art

Over the past few decades, advances have been made in the diagnosis and treatment of vascular defects and abnormalities, such as aneurysms, fistulas, lesions, and other conditions affecting a person's blood vessels and/or internal organs. In some cases, conventional braided wire stents and grafts are used to address these conditions in a patient's vasculature. Transluminal prostheses are well known in the medical arts for implantation in blood vessels, biliary ducts, or other similar organs of the living body. These prostheses are commonly known as stents and are used to maintain, open, or dilate tubular strictures or to support tubular structures. When biocompatible materials are used as a covering or lining for the stent, the prosthesis is called a stent-graft or vascular graft.

An aortic aneurysm, for example, is a weak area in the aorta, which is the main blood vessel that carries blood from the heart to the rest of the body. Weaknesses in the aortic wall may be caused by medical conditions, such as arteriosclerosis. As blood flows through the aorta, the weak vessel wall thins over time and expands like a balloon, which can eventually burst if the vessel wall gets too thin.

Once an aneurysm reaches about 5 cm in diameter, it is usually considered necessary to treat the aneurysm in an effort to prevent it from rupturing. Below 5 cm, the risk of the aneurysm rupturing is lower than the risk of conventional heart surgery in patients with normal surgical risks. The goal of therapy for aneurysms is to prevent the aorta from rupturing. Once an aortic aneurysm has ruptured, the chances of survival are low. Death may be avoided, however, if the aneurysm is detected and treated at an early stage, ideally when the aneurysm is smaller than about 5 cm, using a lower risk procedure.

Aneurysms may be treated with surgery. The surgical procedure for treating some types of aortic aneurysms involves replacing the affected portion of the aorta with a synthetic graft, usually comprising a tube made out of an elastic material with properties very similar to that of a normal, healthy aorta. Surgical treatment is complex, however, and may pose additional risks to the patient, especially the elderly.

More recently, instead of performing surgery to repair an aneurysm, an endovascular stent-graft may be delivered to the site of the aneurysm using elongated catheters. An endovascular stent-graft is a tube that includes a blood-impervious fabric supported by a metal mesh. It can be used to treat a variety of conditions involving blood vessels, but most commonly is used to reinforce a vessel wall at the site of an aneurysm.

To deliver a stent-graft to a target site in a patient's vasculature, typically, the surgeon will make a small incision in the patient's groin area and then insert a delivery catheter or sheath into the vasculature. The delivery sheath usually contains a collapsed, self-expanding or balloon-expandable stent-graft, which is configured to expand to approximately the normal diameter of the aorta at the location of the aneurysm or other abnormality once the stent-graft is deployed from the distal end of the delivery sheath.

The size of the delivery sheath may affect the ability of the surgeon to manipulate the sheath within the patient's vasculature. For example, when the vessel leading to a location of an aneurysm has a diameter that is reduced in size due to arteriosclerosis, larger delivery sheaths may not be used or, at best, may result in trauma to the vascular tissue or may limit treatment options available to some patients. Thus, a smaller delivery sheath may make the treatment available to a larger patient population, lessen the trauma to the vascular tissue, and generally make it easier to accurately deliver and maintain the stent-graft at the proper location. Smaller delivery sheaths also typically allow a physician to access smaller vessels, so as to more proactively treat aneurysms.

For example, a braided, self-expanding stent or a graft incorporating a self-expanding stent as a structural component (referred to herein as a stent-graft) may be introduced into the body by stretching the device axially, until its radial diameter is reduced sufficiently so that it can be fed into a delivery sheath. The device is delivered through the sheath to the site of deployment and then released from the delivery sheath, whereupon the device self-expands to support the patient's vasculature in the location of deployment. A simple delivery device for locating and deploying such a vascular device may include a flexible delivery sheath having a proximal handle and a flexible plunger having a proximal handle. The device is inserted into the distal end of the delivery sheath and the distal end of the delivery sheath is positioned at the site of deployment, such as an artery. The handles of the delivery sheath may be moved relative to each other to push out or uncover the device from the distal end of the sheath.

Because stent-grafts are generally tubular in shape and may lack features at their ends for connecting to a delivery device (such as threads, hooks, etc.), it may be challenging to hold the stent-graft in the contracted state within a delivery device while the delivery device is being positioned at the target site. Likewise, once the delivery device is in position, it may be difficult to deploy the stent-graft from the delivery device or recapture the stent-graft without negatively affecting the configuration of the stent-graft or otherwise impairing the shape or function of the stent-graft.

Accordingly, there is a need for an improved delivery system that provides for a simple and an effective manner of holding a vascular device within the delivery system and allows for the predictable placement of the vascular device within the patient's vasculature, including the ability to reposition or recapture the device prior to full release, such that the shortcomings of conventional solutions are overcome.

SUMMARY OF THE INVENTION

Embodiments therefore provide a delivery device for delivering a vascular device to a target site. In general, the delivery device may be configured to both maintain a proximal portion of a vascular device within a tubular sleeve while the delivery device and vascular device are within a delivery sheath and being positioned at the target site and subsequently to urge the proximal portion of the vascular device out of the tubular sleeve so as to deploy the vascular device at the target site. At the same time, embodiments of the delivery device maintain the ability to recapture the vascular device within a delivery sheath, for example, prior to the full deployment of the proximal portion of the vascular device from the tubular sleeve.

In one embodiment, a device is provided that is configured to deliver a vascular device within a body lumen. The delivery device may include a tubular sleeve, an inner member, and a free-floating ring. The tubular sleeve may define a distal opening, and the inner member may be at least partially disposed within the tubular sleeve and may be configured to move axially therein. The inner member may define a proximal end and a distal end, and the inner member may comprise a stop fixedly disposed proximate the distal end and a band of increased thickness fixedly disposed at a predetermined distance from the stop, such that the band is proximally disposed with respect to the stop. The free-floating ring may be slideably received on the inner member and may be configured to slide along the inner member between the stop and the band. The tubular sleeve and the inner member may be configured to receive a proximal portion of a vascular device therebetween such that, when the stop is disposed within the tubular sleeve, the proximal end of the vascular device is maintained within the tubular sleeve. Thus, when the inner member is moved relative to the tubular sleeve, the free-floating ring may be configured to cooperate with the band to push the proximal end of the vascular device through the distal opening of the tubular sleeve to deploy the vascular device.

In some cases, the predetermined distance between the band and the stop is greater than an axial length of the tubular sleeve. A distal portion of the vascular device may extend distally from the distal opening of the tubular sleeve. The free-floating ring may define a circular void via which the free-floating ring is slideable along the inner member, and the void may define a void diameter that is smaller than an outer diameter of the band and is smaller than an outer diameter of the stop, such that the free-floating ring is maintained on the inner member between the band and the stop. The free-floating ring may define a proximal surface and a distal surface, and the proximal surface may be configured to abut a corresponding surface of the band so as to cause the free-floating ring to move with the band in response to relative distal movement of the inner member with respect to the tubular sleeve. The distal surface of the free-floating ring may be configured to engage the proximal end of the vascular device to push the vascular device out of the distal opening of the tubular sleeve in response to continued relative distal movement of the inner member with respect to the tubular sleeve.

The stop may, in some cases, define an outer diameter that is smaller than an inner diameter of the tubular sleeve, such that, when the stop is disposed within the tubular sleeve, an annular clearance is defined between the stop and an inner surface of the tubular sleeve. The tubular sleeve may be configured to receive a proximal portion of a vascular device comprising a section of increased thickness, and a wall thickness of the vascular device at the section of increased thickness may be greater than the annular clearance defined by the tubular sleeve, such that the proximal portion of the vascular device is retained within the tubular sleeve when the stop is disposed within the tubular sleeve. In some cases, at least one of the stop or the band may be integral to the inner member. The inner member may also define a lumen configured to receive a guidewire therethrough.

In some embodiments, the delivery device may comprise an intermediate tubular member, and a proximal end of the tubular sleeve may be configured to engage a distal end of the intermediate tubular member. The tubular sleeve may comprise an adapter configured to couple the intermediate tubular member and the tubular sleeve together, and the adapter may comprise a distal portion defining a first outer diameter, a proximal portion defining a second outer diameter, and a transition portion therebetween. The first outer diameter may correspond to an inner diameter of the tubular sleeve and the second outer diameter may correspond to an inner diameter of the intermediate tubular member. In some cases, the delivery device may be configured to be axially moveable through a delivery sheath. Additionally or alternatively, the band of increased thickness may be a first band of increased thickness, and the inner member may comprise a second band of increased thickness fixedly disposed at a predetermined distance between the first band and the stop. The second band of increased thickness may be configured to engage a distal surface of the free-floating ring when the inner member is moved in a proximal direction with respect to the tubular sleeve.

In other embodiments, a device for deploying a vascular device within a body lumen is provided that comprises a tubular sleeve configured to radially constrain a proximal portion of a self-expanding vascular device and an inner member defining a proximal end and a distal end and at least partially disposed within the tubular sleeve and configured to move axially therein. The tubular sleeve may define a distal opening, and the inner member may comprise a stop disposed proximate the distal end of the inner member and configured to move with the inner member. The inner member may be configured to move, independently of a proximal portion of the vascular device, between a first position, in which the stop is positioned within the distal opening so as to at least partially block the distal opening of the tubular sleeve, and a second position, in which the stop is disposed outside the tubular sleeve and distally of the distal opening. When the inner member is in the first position, the inner member and tubular sleeve may be configured to cooperate to maintain the proximal portion of the vascular device within the tubular sleeve. When the inner member is in the second position, relative distal movement of the inner member with respect to the tubular sleeve may allow the vascular device to be deployed from the distal opening of the tubular sleeve.

In some cases, the inner member may comprise at least one band of increased thickness that is disposed proximally from, and at a predetermined distance from, the stop. The at least one band of increased thickness may be configured to move with the inner member. The delivery device may also comprise a free-floating ring disposed on the inner member and configured to slide axially along the inner member between the at least one band and the stop within the tubular sleeve. The band may be configured to engage with the free-floating ring such that the band and the free-floating ring move distally together. Furthermore, the free-floating ring may comprise a distal surface configured to engage a proximal end of the vascular device and to deploy the proximal portion of the vascular device from the distal opening of the tubular sleeve when the band, the proximal end of the vascular device, and the free-floating ring are engaged and the inner member is moved distally with respect to the vascular device.

In still other embodiments, a method for deploying a vascular device within a body lumen is provided. The method includes providing a delivery device that comprises a tubular sleeve defining a distal opening, an inner member at least partially disposed within the tubular sleeve and configured to move axially therein, and a free-floating ring slideably received on the inner member. The inner member may define a proximal end and a distal end, and the inner member may comprise a stop fixedly disposed proximate the distal end and a band of increased thickness fixedly disposed at a predetermined distance from the stop, such that the band is proximally disposed with respect to the stop. The free-floating ring may be configured to slide along the inner member between the stop and the band. A proximal portion of a vascular device may be disposed between the tubular sleeve and the inner member, such that a proximal end of the vascular device is positioned between the free-floating ring and the stop and the inner member is disposed in a first position, in which the stop is positioned so as to at least partially block the distal opening of the tubular sleeve.

The method may further include positioning the delivery device and the vascular device within a body lumen and moving the inner member, independently of the proximal portion of the vascular device, from the first position to a second position, in which the stop is disposed distally of the distal opening of the tubular sleeve. The method may also include deploying the proximal portion of the vascular device from the distal opening of the tubular sleeve.

In some cases, deploying the proximal portion of the vascular device may include continuing to distally advance the inner member with respect to the tubular sleeve after the stop is clear of the distal opening so as to move the band into engagement with the free-floating ring and to move the free-floating ring into engagement with the proximal end of the vascular device. In addition, positioning the delivery device and the vascular device within the body lumen may comprise moving the delivery device through the body lumen over a guidewire.

A device loader may be provided in some cases, and the device loader may be coupled to the delivery device and moved distally with respect to the inner member to at least partially constrain a distal portion of the vascular device. Furthermore, a delivery sheath may be positioned within the body lumen proximate a target site and a distal end of the device loader may be connected to a proximal end of the delivery sheath. Positioning the delivery device and the vascular device within the body lumen may include moving the delivery device distally with respect to the delivery sheath. In addition, positioning the delivery device and the vascular device within the body lumen may further comprise at least partially recapturing the vascular device within the delivery sheath by moving the inner member from the second position to the first position prior to full deployment of the proximal portion of the vascular device and moving the delivery device proximally with respect to the delivery sheath.

In some cases, the vascular device may be at least partially recaptured within the delivery sheath by moving the delivery device proximally with respect to the delivery sheath prior to full deployment of the proximal portion of the vascular device. Moreover, the delivery device may be withdrawn from the body lumen after the vascular device is deployed.

In still further embodiments, a system for delivering a vascular device within a body lumen may be provided. The system may include a delivery device, a delivery sheath defining a lumen configured to receive the delivery device therethrough, and a device loader. The delivery device may include a tubular sleeve defining a distal opening, an inner member at least partially disposed within the tubular sleeve and configured to move axially therein, and a free-floating ring. The inner member may define a proximal end and a distal end, and the inner member may comprise a stop fixedly disposed proximate the distal end and a band of increased thickness fixedly disposed at a predetermined distance from the stop, such that the band is proximally disposed with respect to the stop. In addition, the free-floating ring may be slideably received on the inner member and may be configured to slide along the inner member between the stop and the band.

The device loader may be configured to slideably extend about a portion of the delivery device so as to at least partially constrain a distal portion of a vascular device to allow the vascular device to be received within the lumen of the delivery sheath. The delivery sheath may be configured to be positioned within the body lumen proximate a target site, and the tubular sleeve and the inner member of the delivery device may be configured to receive a proximal portion of the vascular device therebetween such that, when the stop is disposed within the tubular sleeve, the proximal end of the vascular device is maintained within the tubular sleeve. The delivery device and the received vascular device may be configured to be moved distally through the lumen of the delivery sheath toward the target site. Furthermore, the inner member may be moved relative to the tubular sleeve, and the free-floating ring may be configured to cooperate with the band to push the proximal end of the vascular device through the distal opening of the tubular sleeve to deploy the vascular device.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

FIG. 3 is a partially exploded view of a proximal portion and a distal portion of a delivery device according to an exemplary embodiment;

FIG. 4 is a detail partially exploded view of the distal portion of the delivery device of FIG. 3 according to an exemplary embodiment;

FIGS. 6A-6D illustrate deployment of a vascular device from the distal portion of the delivery device of FIG. 5 according to an exemplary embodiment.

DETAILED DESCRIPTION

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments provide a device for delivering a vascular device to a target site within a body lumen. As described in greater detail below, the vascular device may be, for example, a tubular stent-graft configured to support and/or occlude an abnormality or defect in a patient's vasculature, such as an aneurysm. For example, the vascular device may be a multi-layer device and may in some cases include one or more occluding layers. An example of a multi-layer device that may be delivered using embodiments of the delivery device described herein is discussed in the co-pending application titled *Device and Method for Treating Vascular Abnormalities*, filed concurrently herewith, the contents of which are incorporated by reference herein.

Figure 1A:
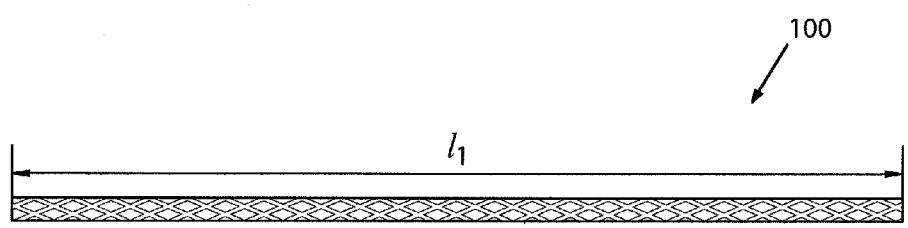
FIG. 1A is a schematic illustration of a vascular device in a contracted state according to an exemplary embodiment.
Figure 1B:
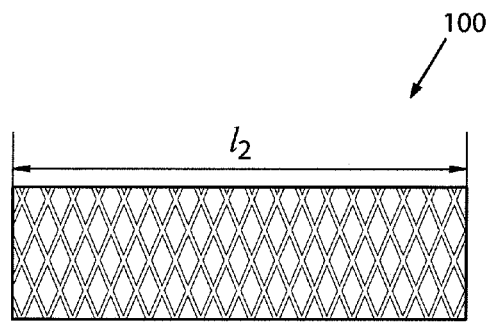
FIG. 1B is a schematic illustration of a vascular device in an expanded state according to an exemplary embodiment.

A vascular device that may be delivered using embodiments of the delivery device discussed below may, for example, be a self-expanding vascular device that is configured to move between a contracted state when constrained within the delivery device and an expanded state when deployed from the delivery device for delivery to a target site within the body lumen. With reference to FIGS. 1A and 1B, the vascular device 100, which may be, for example, a stent, a graft, or a stent-graft, may have a contracted state (FIG. 1A) defining a length $l_1$ when constrained within the delivery device and an expanded state (FIG. 1B) defining a length $l_2$ when deployed from the delivery device at a target site within the body lumen (e.g., the site of an aneurysm). For example, a vascular device having a predetermined shape may be collapsed by longitudinally stretching the vascular device (as illustrated in FIG. 1A) and inserting the vascular device into the lumen of the delivery device, as described in greater detail below. The delivery device may then be positioned and advanced in a patient's body such that the distal end of the delivery device is adjacent to the target site. As the vascular device 100 is deployed from a delivery device, the diameter of the vascular device expands and draws the ends of the device closer to each other. In other words, the length $l_2$ of the vascular device when it is in an expanded state (e.g., deployed from the delivery device) is shorter than the length $l_1$ of the vascular device when it is in a contracted state (e.g., undeployed from the delivery device).

It is understood that the use of the term "target site" is not meant to be limiting, as the delivery device may be configured to deliver a vascular device to any target site, such as an abnormality, a vessel, an organ, an opening, a chamber, a channel, a hole, a cavity, or the like, located anywhere in the body. The term "vascular abnormality," as used herein is not meant to be limiting, as the vascular device 100 may be configured to bridge or otherwise support a variety of vascular abnormalities. For example, the vascular abnormality could be any abnormality that affects the shape of the native lumen, such as an aneurysm, a lesion, a vessel dissection, or a tumor.

In some cases, embodiments of the vascular device may be useful in the vessels of a patient's thoracic area. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to an aneurysm. Furthermore, the term "vascular device" is used herein to describe, according to embodiments of the present invention, a braided, self-expanding stent or a graft incorporating a self-expanding stent as a structural component.

As noted above, once the delivery device is in position at the target site, the vascular device may be urged through the delivery device and out the distal end of the delivery device, whereupon it may substantially return to its expanded state (as illustrated in FIG. 1B). The delivery device may then be removed from the patient's body, leaving the vascular device positioned at the target site.

Figure 2:
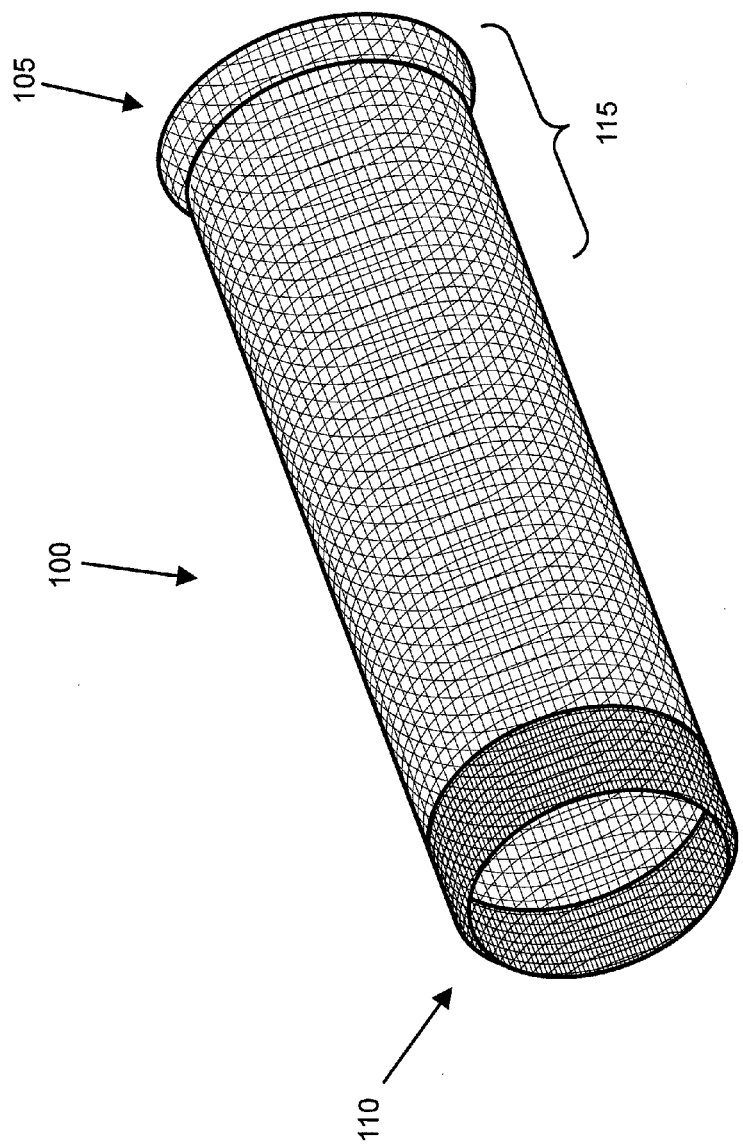
FIG. 2 is a perspective view of a vascular device in an expanded state according to an exemplary embodiment.

Referring to FIG. 2, the vascular device 100 that may be delivered using embodiments of the delivery device described herein may define a proximal end 105 and a distal end 110 in the contracted state and in the expanded state, as well as in states in between the contracted and expanded states (e.g., in the process of being deployed from a delivery device, when, for example, part of the vascular device is in the contracted state and part of the vascular device is in the expanded state). As used herein, the term "proximal" refers to a part of the vascular device 100 or the delivery device or delivery assembly that is closest to the operator (e.g., the surgeon or interventionalist), and the term "distal" refers to a part that is farther from the operator at any given time as the vascular device is being delivered through the delivery device.

When positioning a vascular device having or incorporating a generally tubular configuration, such as the vascular device 100 of FIGS. 1A, 1B, and 2, it is desirable to secure the vascular device 100 within the delivery device while the delivery device and vascular device are being moved through the body lumen for appropriate positioning at the target site. At the same time, once a distal end of the vascular device has been positioned near the distal end of the delivery sheath adjacent the target site, it is also desirable to effectively urge the vascular device 100 out of the delivery sheath without impairing the configuration of the vascular device (e.g., the shape or arrangement of the layers) while at the same time allowing for the recapture of the vascular device within the delivery sheath in the event the vascular device must be repositioned, for example, before the vascular device has been fully deployed. The securement and subsequent deployment of the vascular device 100 may be particularly challenging when one or both ends of the vascular device do not include connecting features (such as threads or hooks) that would facilitate its attachment to part of the delivery device.

Accordingly, embodiments of a delivery device are provided that are configured to both maintain a proximal portion of a vascular device within a tubular sleeve while the delivery device and vascular device are within a delivery sheath and being positioned at the target site and subsequently to urge the proximal portion of the vascular device out of the tubular sleeve so as to deploy the vascular device at the target site. At the same time, embodiments of the delivery device maintain the ability to recapture the vascular device within a delivery sheath, for example, prior to the full deployment of the proximal portion of the vascular device from the tubular sleeve.

Referring now to FIG. 3, a delivery device 150 is shown for delivering a vascular device (such as the vascular device 100 of FIG. 2) within a body lumen. The delivery device 150 may be configured to interact with and/or cooperate with other delivery tools and accessories, such as vascular device loaders, delivery sheaths/catheters, dilators, guidewires, etc., some of which are described in further detail below. In addition, one skilled in the art in view of this disclosure would recognize that the delivery device 150 shown in FIG. 3 is representative of numerous different configurations that may be used. For example, although FIG. 3 shows a certain number and type of connections and ports, as described in greater detail below, other connections, ports, valves (e.g., hemostasis valves), and delivery device components may be included in the delivery device to facilitate the introduction of the delivery device and vascular device into the body lumen.

An embodiment of the delivery device 150 is shown in FIGS. 3 and 4, in which the components are not assembled for illustrative purposes. In the embodiment shown in FIG. 3, the delivery device 150 includes a distal portion 200 configured to engage the proximal end 105 of the vascular device 100 (e.g., shown in FIG. 2) and a proximal portion 300. The proximal portion 300 may, for example, include one or more hubs 310 configured to connect different parts of the delivery device 150 to each other and/or one or more Y-connectors 320 having a port 325 configured to allow the introduction of a saline solution to parts of the delivery device and the vascular device to prepare the delivery device and vascular device for entry into the body lumen. The proximal portion 300 may also have features to facilitate the handling and operation of the delivery device 150 by an operator, such as a handle 330 with a locking knob 335, described below.

The distal portion 200 of the delivery device 150 is shown in greater detail in FIG. 4. The distal portion 200 of the delivery device 150 may include a tubular sleeve 205, an inner member 220, and a free-floating ring 210 that cooperate, as described below, to engage and maintain a proximal portion 115 of the vascular device 100 (shown in FIG. 2) within the tubular sleeve for delivery of the vascular device to the target site. The inner member 220 may be configured for applying an axial force on the proximal portion 115 of the vascular device 100 to urge the vascular device out of the delivery sheath for deployment. In this regard, the inner member 220 may comprise a material that resists buckling when a compressive force is applied along the axis of the inner member and can withstand tensile forces that may be applied when the vascular device is collapsed (e.g., for insertion into the body), but at the same time is somewhat flexible to allow the delivery device to traverse the patient's vasculature. For example, the inner member 220 may comprise a stainless steel hypo-tube in some embodiments. The inner member 220 may extend or be connected to other tubular members that extend the length of the delivery device 150, such that a user, through manipulation of the proximal portion 300 of the delivery device, may be able to deploy the vascular device 100 from the distal portion 200 at the target site. For example, in some embodiments, the inner member 220 may extend through a hub 310, wherein the inner member may be joined to a more rigid tubular member 340 configured to facilitate the operator's handling of the delivery device 150, as shown in FIG. 3.

In this regard, in some embodiments, the inner member 220 may define a proximal end 250 (shown in FIG. 3) and a distal end 255 (e.g., shown in FIGS. 3 and 4). The inner member 220 may comprise a nub or stop 215 and two protrusions or bands 225, 235 of increased thickness that are fixedly disposed on the inner member 220. Turning to FIG. 5, which shows the distal portion 200 in an assembled configuration, for example, the stop 215 may be attached (e.g., welded) or, in some embodiments, may be integral to, the inner member 220 proximate the distal end 255, and the bands 225, 235 may be attached (e.g., welded) or integral to the inner member at predetermined distances from the stop 215, such that the stop is completely outside the tubular sleeve 205 when the band 225 first engages the free-floating ring 210. The first band 225 and the second band 235 may be positioned on the inner member 220 proximally with respect to the stop 215, but on either side of the free-floating ring 210. Thus, when the inner member 220 is moved distally with respect to the tubular sleeve 205 and the stop 215 is removed from within the tubular sleeve, the first band 225 may urge the free-floating ring 210 toward the distal end 255. When the inner member 220 is moved proximally with respect to the tubular sleeve 205 and the stop 215 is completely within the tubular sleeve, the second band 235 may urge the free-floating ring 210 toward the proximal end of the tubular sleeve. In other words, the first and second bands 225, 235 may act as limits to the movement of the free-floating ring 210 along the inner member 220. In some cases, the second band 235 may be optional; however, in other cases, the second band 235 may be useful as a manufacturing aid to facilitate the positioning of the free-floating ring 210 during loading of vascular device 100.

As shown in the assembled configuration of FIG. 5, the inner member 220 may be at least partially disposed within the tubular sleeve 205 and may be configured to move axially therein, such that the stop 215 and the bands 225, 235 are configured to move with the inner member 220. The free-floating ring 210, in contrast, includes an opening (e.g., a circular void 211, shown in FIG. 5A) that is larger than the outer diameter of the inner member 220 and smaller than the outer diameter of the bands 225, 235. The free-floating ring 210 may be configured to be slideably received on the inner member 220 so as to be able to slide axially along the inner member between the first band 225 and the second band 235, as noted above. In other words, while movement of the inner member 220 necessarily results in movement of the stop 215 and the bands 225, 235, the free-floating ring 210 may not necessarily be moved upon movement of the inner member 220 and is, in some respects, independent of the inner member 220 within the limits created by the bands 225, 235.

Thus, referring to FIG. 6A, the tubular sleeve 205 and the inner member 220 may be configured to engage the proximal portion 115 of the vascular device 100 therebetween, with the proximal end 105 of the vascular device located between the free-floating ring 210 and the stop 215. In this way, when the stop 215 is disposed within the tubular sleeve 205, as shown in FIG. 6A, the proximal end 105 of the vascular device 100 is maintained within the tubular sleeve 205, while the distal portion extends outwardly and distally from the tubular sleeve in the expanded state when not maintained in the contracted state by a device loader 400 or a delivery sheath, as described below.

The tubular sleeve 205, in turn, may be configured to radially constrain the proximal portion 115 of the vascular device 100. The tubular sleeve 205 may define a distal opening 230 at a distal end thereof, and the remainder of the vascular device 100 (i.e., the portion of the vascular device not contained within the tubular sleeve) may extend out of the distal opening. Depending on the size of the vascular device 100, about 5%-10% or more of the length of the device (in the constrained state) may be held within the tubular sleeve 205.

Referring now to FIGS. 6A-6D, the inner member 220 may be configured to move between a first position (shown in FIG. 6A), in which the stop 215 is positioned within the tubular sleeve 205 (e.g., at or slightly recessed from or proximal to the distal opening 230) so as to at least partially block the distal opening 230 of the tubular sleeve 205, and a second position (shown in FIG. 6B), in which the stop is disposed outside (i.e., distally of) the tubular sleeve and is clear of the distal opening. When the inner member 220 is in the first position (FIG. 6A), the inner member and tubular sleeve 205 may be configured to cooperate to maintain the proximal portion 115 of the vascular device within the tubular sleeve. When the inner member 220 is in the second position (FIG. 6B), however, distal movement (i.e., movement in the direction D) of the inner member with respect to the tubular sleeve 205 can serve to allow the deployment of the vascular device 100 from the distal opening 230 of the tubular sleeve (FIGS. 6C and 6D). In other words, the inner member 220 is configured to move independently of the proximal portion 115 of the vascular device 100 between the first position and the second position, as shown in FIGS. 6A and 6B, and is also configured such that continued distal movement of the inner member 220 relative to the tubular sleeve 205 effects the deployment of the vascular device 100 from the tubular sleeve 205. This occurs because the band 225 contacts the free-floating ring 210 and, in turn, the free-floating ring contacts the proximal end of the vascular device 100, as described in greater detail below. In this regard, relative distal movement may be effected by the operator through proximal movement of the tubular sleeve 205 with respect to the inner member 220 to deploy the vascular device 100.

Accordingly, various parts of the tubular sleeve 205, inner member 220, stop 215, free-floating ring 210, and bands 225, 235 may be dimensioned relative to each other to allow for the components to interact when the inner member is moved distally relative to the tubular sleeve 205 (in the direction D) out of the distal opening 230 of the tubular sleeve, as described above. For example, in some embodiments, the predetermined distance between the band 225 and the stop 215 is greater than an axial length l of the tubular sleeve 205. As a result, relative distal movement of the inner member 220 with respect to the tubular sleeve 205 can serve to move the stop 215 distally out of the tubular sleeve 205 for at least some distance (see FIG. 6B) before the band 225 engages and begins moving the free-floating ring 210 (see FIG. 6C).

In addition, the outer diameter $od_r$ of the free-floating ring 210 (shown in FIG. 5A) may be approximately equal to, but slightly smaller than, an inner diameter $id_{ts}$ of the tubular sleeve 205, such that the clearance between the outer circumferential edge of the ring and the inner surface of the tubular sleeve is less than the wall thickness of the vascular device 100 at the proximal end. Likewise, the void 211 of the free-floating ring 210 may have a diameter $d_v$ that is approximately equal to, but slightly larger than, an outer diameter $od_{im}$ of the inner member 220, thereby facilitating the movement of the free-floating ring along the inner member between the first band 225 and the second band 235.

Figure 5A:
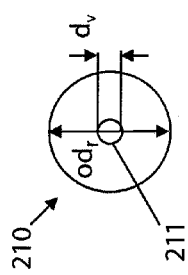
FIG. 5A is a detail cross-sectional view of a free-floating member of the delivery device of FIG. 5 taken in a transverse plane according to an exemplary embodiment.
Figure 5:
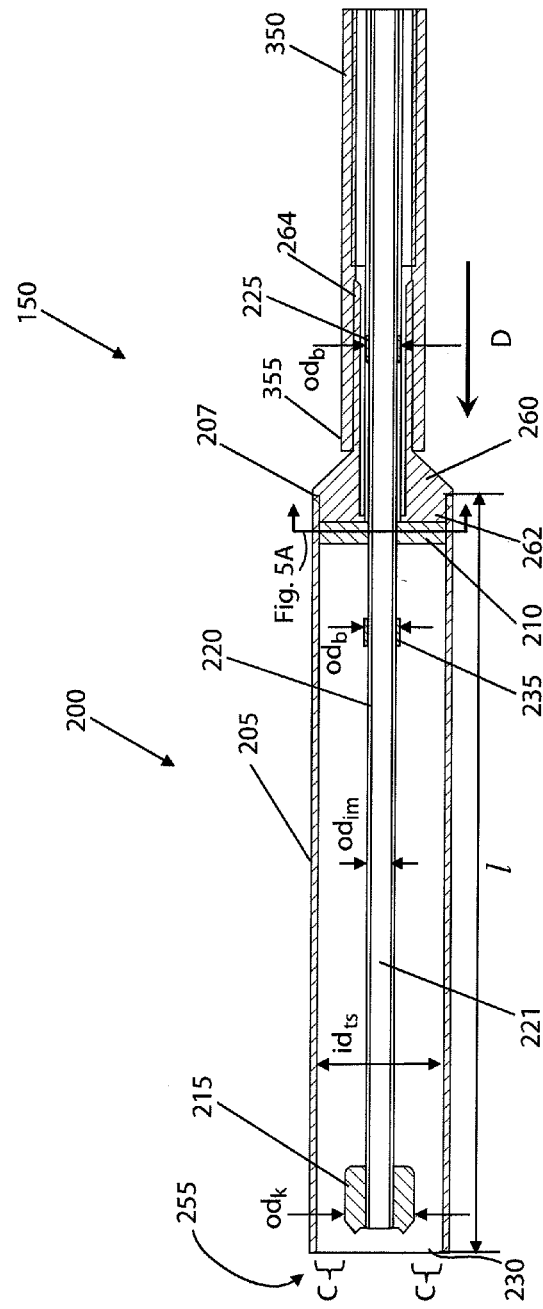
FIG. 5 is a cross-sectional view of the distal portion of the delivery device of FIG. 4 in an assembled configuration according to an exemplary embodiment.

Furthermore, the void diameter $d_v$ defined by the void 211 of the free-floating ring 210 may be sized smaller than an outer diameter $od_b$ of the bands 225, 235 as illustrated in FIGS. 5 and 5A. In this way, the axial movement of the free-floating ring 210 can be limited in a distal direction by the second band 235 and in the proximal direction by the first band 225, thereby maintaining the free-floating ring on the inner member between the two bands. Moreover, the relative sizing of the void 211 with respect to the first band 225 is such that as the first band is moved relatively distally in the direction D with the inner member 220 (FIGS. 6A-6C), the first band may engage the free-floating ring 210 and, upon continued relative distal movement of the inner member, the first band and the free-floating ring may cooperate to push the proximal end of the vascular device through the distal opening 230. Conversely, the relative proximal movement of the inner member 220 may allow the second band 235 to engage a distal side of the free-floating ring 210 and allow for the placement of the free-floating ring adjacent the proximal end of the tubular sleeve 205 to facilitate the initial loading of the vascular device 100 at the factory, for example.

In this regard, with reference to FIG. 6B, the free-floating ring 210 may define a proximal surface 212 and a distal surface 213. The proximal surface 212 may be configured to abut a corresponding surface 227 of the first band 225 so as to cause the free-floating ring to move with the first band when the inner member 220 is moved distally with respect to the tubular sleeve 205 (e.g., once sufficient distal movement of the inner member and the first band has taken place, as shown in FIG. 6C). As the inner member 220 continues to be moved distally with respect to the tubular sleeve 205, the distal surface 213 of the free-floating ring 210 may in turn be configured (e.g., through the relative dimensions described above) to engage the proximal end 105 of the vascular device 100 to push the vascular device out of the distal opening 230 of the tubular sleeve, as illustrated in FIGS. 6C and 6D. In other words, the proximal portion 115 of the vascular device may be deployed from the tubular sleeve 205 when the first band 225, the proximal end of the vascular device, and the free-floating ring are engaged and the inner member 220 is moved distally.

Figure 7:
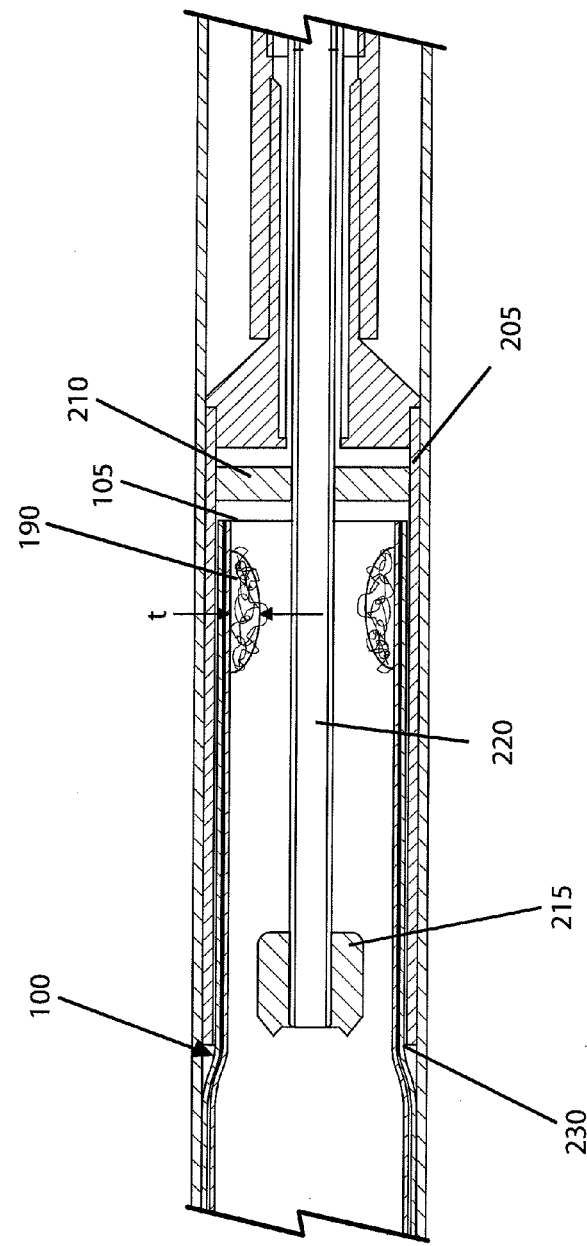
FIG. 7 is a cross-sectional view of a vascular device with an occluding structure having a section of increased thickness positioned within the distal portion of the delivery device of FIG. 5 according to an exemplary embodiment.

Turning again to FIG. 5, in some embodiments, the stop 215 defines an outer diameter $od_k$ that is smaller than the inner diameter $id_{ts}$ of the tubular sleeve 205, such that, when the stop is disposed within the tubular sleeve (e.g., when the stop is in the first position, shown in FIG. 6A), an annular clearance C is defined between the stop and the inner surface of the tubular sleeve. The proximal portion 115 of the vascular device 100 may in turn define a section of increased thickness 190, as shown in FIG. 7, having a wall thickness t that may be greater than the annular clearance C such that the proximal portion 115 of the vascular device is retained within the tubular sleeve 205 when the stop 215 is disposed within the tubular sleeve. In some cases, the section of increased thickness 190 may be a suture stitched into the vascular device (e.g., holding an occluding layer to an inner layer of the vascular device), a marker band for allowing radioscopic monitoring of the location of the proximal end of the vascular device, or any other feature that increases a localized thickness of the vascular device near the proximal end 105 of the vascular device.

The tubular sleeve 205 may thus be configured to receive the proximal portion 115 of the vascular device 100, where the proximal portion includes the section of increased thickness 190. By moving the inner member 220 distally from the first position (FIG. 6A) to the second position (FIG. 6B), the distal opening 230 may be cleared, and the proximal portion 115 of the vascular device 100, including the section of increased thickness 190, may be urged out of the tubular sleeve 205.

Referring to FIG. 3, and as noted above, in addition to the distal portion 200 discussed above in connection with FIGS. 4-7, the delivery device 150 may also include a proximal portion 300. In some embodiments, the proximal portion 300 of the delivery device 150 may include an intermediate tubular member 350. The intermediate tubular member 350 may, for example, be a poly-braided shaft defining a lumen through which the inner member 220 may extend. The intermediate tubular member 350 may be configured to have sufficient axial stiffness and compression resistance to handle the forces encountered during device delivery, repositioning, and/or recapture.

As illustrated in FIG. 4, the distal portion 200 of the delivery device 150 may include an adapter 260 that is configured to join the tubular sleeve 205 to the intermediate tubular member 350. In this regard, the adapter 260 may include a distal portion 262 defining a first outer diameter $d_1$ and a proximal portion 264 defining a second outer diameter $d_2$. The first outer diameter $d_1$ may correspond to an inner diameter of the tubular sleeve 205, and the second outer diameter $d_2$ may correspond to an inner diameter of the intermediate tubular member 350. A transition portion 266 may extend between the distal portion 262 and the proximal portion 264, and the transition portion may include a taper from the first outer diameter $d_1$ to the second outer diameter $d_2$.

The distal portion 262 may be configured to fit into the proximal end 207 of the tubular sleeve 205 (as shown in FIG. 5), and as such the first outer diameter $d_1$ may correspond to the inner diameter $id_{ts}$ of the tubular sleeve. The adapter 260 may, for example, be welded or otherwise attached to the proximal end 207 of the tubular sleeve 207. Similarly, the proximal portion 264 of the adapter 260 may be configured to fit into the distal end 355 of the intermediate tubular member 350. In some cases, the proximal portion 264 may include ribs 268 or other protrusions, and the proximal portion may be engaged with the intermediate tubular member 350 through a heat shrinking process or alternatively may be bonded to the intermediate tubular member using an adhesive.

With reference to FIG. 3, the proximal end of intermediate tubular member 350 may be connected to a connector 310 having a lumen therethrough by use of adhesives or heat shrink tubing, as known in the art. The proximal end of the connector 310 may be threaded to connect to mating threads on a connector 320, such as a Y-adapter with a side arm lumen in fluid communication with the lumen of the intermediate tubular member 350. Additionally, the connector 320 may have a through lumen for the passage of the tubular member 340 and an adjustable Touhy-Borst adapter to seal against the rigid tubular member 340, which may be a proximal connected extension of the inner member 220. When the Touhy-Borst adapter is tightened against the rigid tubular member 340, the inner tubular member 220 may, in essence, be attached to the intermediate tubular member 350, provided the connectors 310, 320 are threaded together, thereby facilitating the proximal and distal movement of the delivery device as a unit, such as, for example, in delivering a vascular device 100 through a delivery sheath 500 to a target site in the body.

As noted above, the delivery device 150 may be configured to be used as part of a delivery system or assembly that includes other delivery tools and accessories designed to facilitate the insertion, positioning, and deployment of the vascular device 100. For example, with reference to FIG. 5, the delivery device 150 may be configured for use with a guidewire, and in such cases the inner member 220 may define a lumen 221 that is configured to receive the guidewire therethrough, such as a 0.039 in. diameter guidewire. Thus, as will be recognized by those skilled in the art in view of this disclosure, the delivery device 150 may be routed through a patient's vasculature to a target site over a guidewire that establishes the appropriate path through the vasculature.

Figure 8:
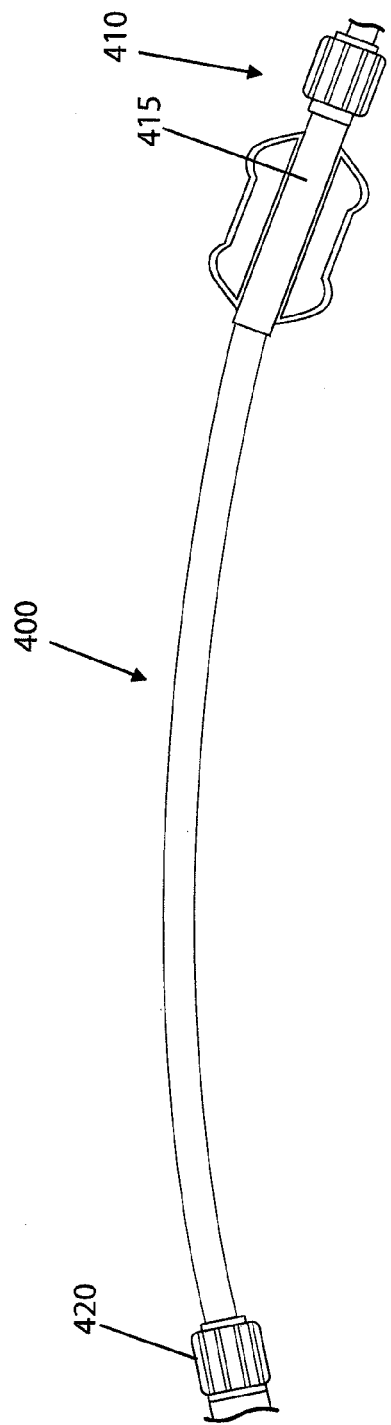
FIG. 8 is a schematic illustration of a device loader that may be used with a delivery device according to an exemplary embodiment.

With regard to a self-expanding vascular device 100 configured to have a contracted state when constrained and an expanded stated when unconstrained, the delivery device 150 may be configured to axially move within a lumen of a device loader 400 (shown in FIG. 8) such that a distal portion of the delivery device and the vascular device 100 connected thereto may be back-loaded into a device loader 400 that is designed to radially constrain the vascular device from the expanded state to the contracted state. The device loader 400 may, for example, comprise a tubular member with a lumen sized for radial constraint and passage therethrough of the vascular device 100 in the contracted state and the intermediate tubular member 350 and may be configured to be attached at its proximal end 410 via a hub (e.g., hub 415) and/or a connector (e.g., a Y-connector with a Tuohy-Borst adapter) for selective connection to a distal portion of the intermediate tubular member 350 of the delivery device 150, as will be recognized by those skilled in the art in view of this disclosure. In this way, relative axial movement between the device loader 400 and the delivery device 150 may be allowed or not allowed, as desired, and a fluid seal against the intermediate tubular member may be formed. The distal end of the device loader 400 may have a distal connector 420 configured for connection to the proximal end of a delivery sheath 500. Connectors 420 and 415 may be sealingly attached to the tubular member using adhesives or heat shrink, as known in the art. For example, an operator may receive the delivery system with the delivery device 150 preloaded through the lumen of the device loader 400 such that the distal portion 200 of the delivery device is adjacent the distal end of the device loader 400, with the proximal portion 115 of the vascular device 100 retained within the tubular sleeve 205 and the remainder of the vascular device 100 extending distally in the expanded state. To fully constrain the vascular device 100 in the contracted state, the operator would first ensure that the Touhy-Borst adapter on the connector 320 is tightened and that the handle 330 on the proximal portion 300 of the delivery device 150 is affixed to the rigid tubular member 340 (and, as a result, to the inner member 220) via the locking knob 335. Then the operator would simply move the device loader 400 distally with respect to the delivery device 150 (e.g., by loosening the Touhy-Borst adapter 410 to allow axial movement relative to the tubular member 350) to collapse the expanded portions of the vascular device 100 in preparation for connection of the device loader 400 to, for example, a delivery sheath 500. The distal movement of the device loader 400 may thus force the collapsed vascular device 100 into the lumen of the device loader to constrain the vascular device. To facilitate introduction of a proximal end of a guidewire through the vascular device 100 and device loader 400, the distal end of the vascular device 100 may extend partially distally from the distal end of the device loader 400 in a partially expanded state (e.g., providing a funnel shape).

Figure 9:
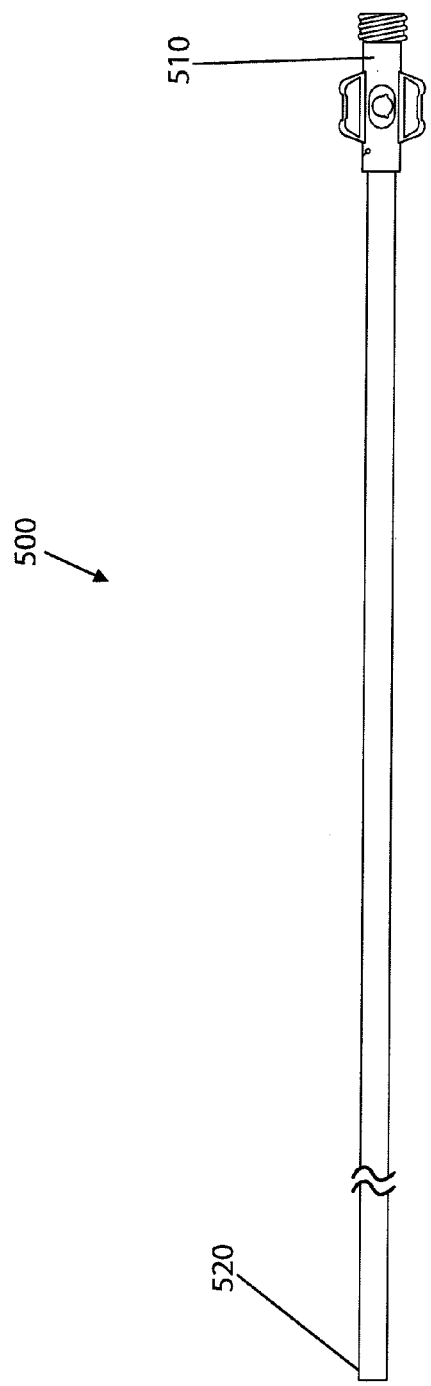
FIG. 9 is a schematic illustration of a delivery sheath that may be used with a delivery device according to an exemplary embodiment.

The delivery sheath 500 (shown in FIG. 9), in turn, may include a corresponding connector, such as a threaded hub 510, which is configured to connect to the distal end of the device loader 400 (e.g., via the distal connector 420). For example, the delivery sheath 500 is typically placed in the body lumen separately by the operator, over a guidewire, to a location adjacent the target site. In preparation for connection of the device loader 400, the operator may feed a proximal end of the guidewire through the funnel-shaped expanded distal portion of the vascular device 100, as previously mentioned, and through the lumen of the inner member 220 and the rigid tubular member 340 until it extends proximally of the proximal end of the delivery device. The device loader 400 may then be used to fully constrain the vascular device 100, such as through the relative distal movement of the device loader 400 with respect to the delivery device 150 as described above, and, once the entire delivery system is flushed with saline, the distal connector 420 (FIG. 8) of the loader 400 may be connected to the proximal end of the delivery sheath 500 (e.g., via the threaded hub 510 shown in FIG. 9). Thus, the use of the device loader 400 to constrain the vascular device 100 and connect to the delivery sheath 500 already in position within the patient's vasculature may serve to establish a pathway for the delivery device 150 and the vascular device to be advanced (e.g., axially moved in the distal direction) through the delivery sheath to the target site.

In this regard, the delivery sheath 500 may be a single lumen tubular structure that, depending on the application (e.g., location of the target site), may be approximately 90 cm in length. The delivery sheath 500 may have a polytetrafluoroethylene (PTFE) liner surrounded by a stainless steel braid, metal coil, or other stiff element, with a layer of polyether block amide (e.g., PEBAX® coating) or other polymer applied thereon that permeates and covers the braid. The distal portion of the delivery sheath 500 in some embodiments may have a tapered tip and may be made of a softer, more flexible material than the proximal portion of the delivery sheath to facilitate the insertion of the delivery sheath into the patient's vasculature and to reduce trauma to the vessel. The lumen of the delivery sheath 500 may vary in diameter, but generally, and as a non-limiting example, may have a diameter of between approximately 4.1 mm for a 12 Fr. outer diameter sheath to approximately 4.8 mm for a 14 Fr. outer diameter sheath or approximately 5.4 mm for a 16 Fr. outer diameter sheath.

Accordingly, the delivery device may be used to deploy a vascular device proximate a target site in a patient's vasculature. Embodiments of methods that may be used to deploy a vascular device, such as a self-expanding stent-graft, are summarized in the flow charts provided in FIGS. 10 and 11.

Figure 10:
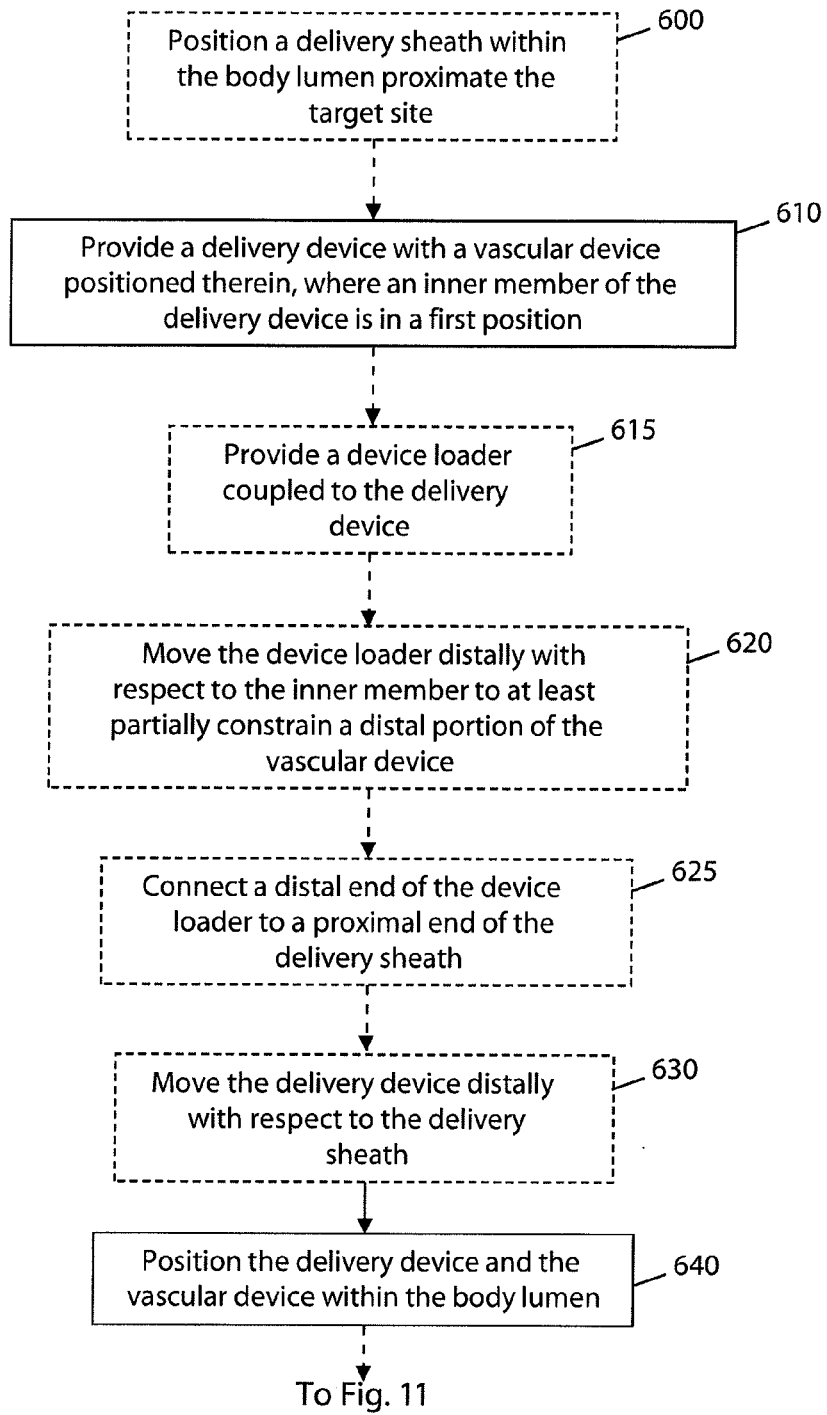
FIGS. 10 and 11 illustrate flowcharts of a method of delivering a vascular device according to an exemplary embodiment.

Initially, a delivery sheath may be placed into the body lumen over a guidewire and advanced to the target site. FIG. 10, Block 600. The distal end of the delivery sheath may be placed just proximal to the most distal position where it is desired that the vascular device contact the vessel wall in the expanded state upon deployment. In this way, the delivery sheath may be in position to deliver the delivery device and the vascular device carried by the delivery device.

In this regard, the delivery device may be provided as described above with reference to FIGS. 3-7. Block 610. For example, the delivery device may include a tubular sleeve defining a distal opening, an inner member at least partially disposed within the tubular sleeve and configured to move axially therein, and a free-floating ring slideably received on the inner member. The inner member may define a proximal end and a distal end, and the inner member may comprise a stop fixedly disposed proximate the distal end and one or more bands of increased thickness fixedly disposed at predetermined distances from the stop, such that the bands are proximally disposed with respect to the stop and act as limits on the movement of the free-floating ring along the inner member. The free-floating ring may thus be configured to slide along the inner member between the two bands, as described above.

As received by the operator from the delivery device manufacturer, the delivery device may be pre-loaded through a device loader (Block 615), and a proximal portion of the vascular device may be pre-loaded into the delivery device and the device loader in a constrained state. The remainder of the vascular device may extend distally from the device loader in an expanded state, as noted above. As such, the proximal portion of the vascular device may be disposed between the tubular sleeve and the inner member, such that a proximal end of the vascular device is positioned between the free-floating ring and the stop and the inner member is disposed in a first position. In the first position, the stop may be positioned at a distal end of the tubular sleeve so as to at least partially block the distal opening of the tubular sleeve, for example, as illustrated in FIG. 6A. The device loader may be moved distally by the operator with respect to the delivery device to collapse and force a distal portion of the vascular device into the device loader and thus at least partially constrain a distal portion of the vascular device. Block 620. A small distal portion may remain expanded to facilitate back-loading of a guidewire through the vascular device and the delivery device lumen.

In this regard, a guidewire may be back-loaded through the vascular device and delivery device, as noted above. The device loader may then be advanced distally with respect to the delivery device to draw the most distal portion of the vascular device into the constrained state within the device loader. The distal end of the device loader may then be connected to the proximal end of the delivery sheath. Block 625. Thus, as shown in FIGS. 6A-6D, the delivery device may be moved distally with respect to the device loader 400 and the delivery sheath 500 to insert the delivery device 150 and the vascular device 100 into the delivery sheath 500 and to thus position the delivery device and the vascular device within the body lumen. Block 630, 640.

Figure 11:
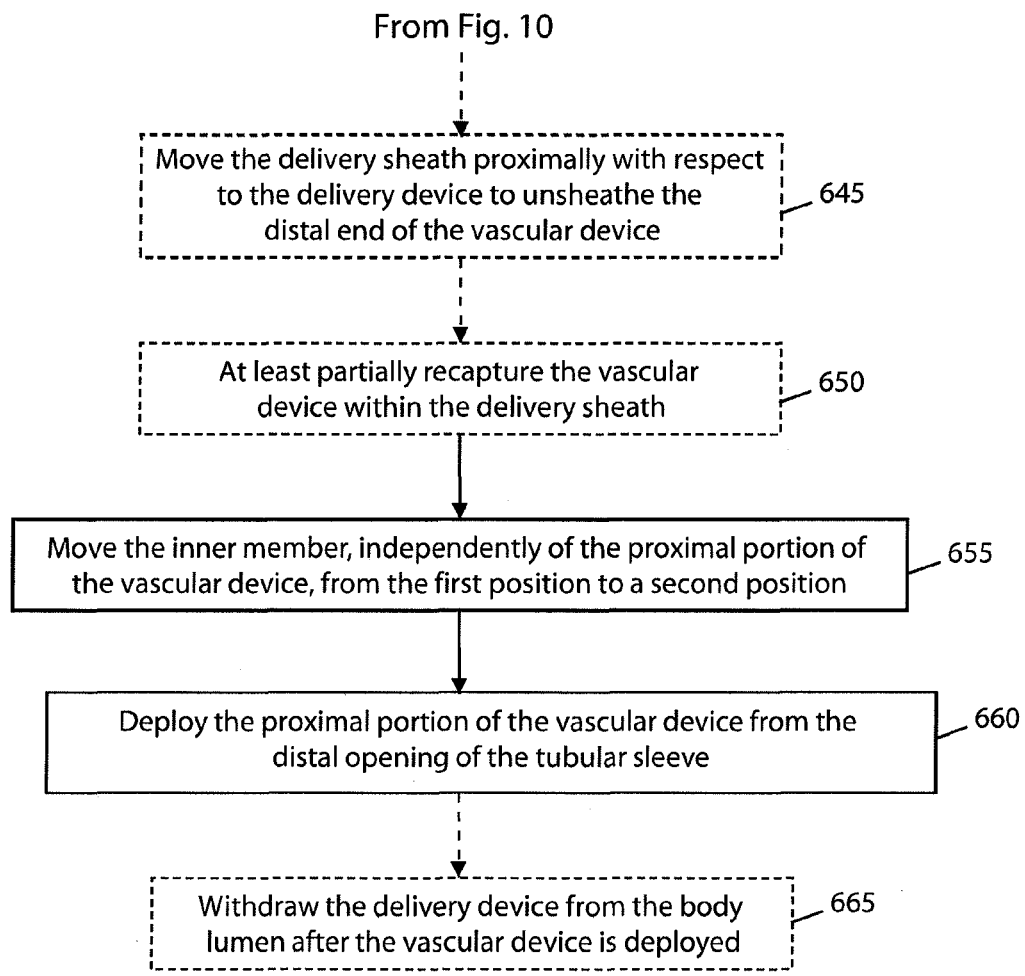

Once the delivery device is positioned such that the vascular device can be deployed proximate the target site, the operator may unsheathe the distal end of the vascular device 100 by moving the delivery sheath 500 proximally with respect to the delivery device 150 (e.g., while holding the delivery device stationary). FIG. 11, Block 645. This allows the vascular device to self-expand against the vessel at the target site.

Once the vascular device is deployed, the proximal end of the delivery sheath may be just proximal to the distal end of the delivery device. Thus, the proximal portion of the vascular device may still be constrained within the tubular sleeve, and the operator can ensure that the distal end of the vascular device is positioned as desired. If repositioning is needed, the vascular device may be retracted back into the delivery sheath by holding the delivery device in place and advancing the delivery sheath distally until the device is fully contained within the delivery sheath. Block 650. Thus, the deployment procedure (and repositioning procedure) may be repeated as needed until the vascular device is in the appropriate position at the target site. If the device is determined to be the wrong size with respect to the target site or must be withdrawn for any other reason, the vascular device (via the delivery device) may be withdrawn from the delivery sheath, and another vascular device may be used in its place in a manner similar to that described above.

To fully deploy the vascular device 100, the operator may move the tubular sleeve 205 proximally relative to the proximal portion 115 of the vascular device 100, from the first position, in which the stop 215 is positioned so as to at least partially block the distal opening 230 of the tubular sleeve 205, to a second position, in which the stop is disposed distally of the tubular sleeve and is clear of the distal opening, as shown in FIG. 6B. Block 655. This may be done, for example, by loosening the locking knob 335 on the handle 330 (shown in FIG. 3) and moving the handle proximally until the handle contacts the proximal end of the rigid member 340. The operator may then retighten the locking knob 335 and, while holding the handle 330 stationary, pull the connectors 310, 340 proximally, thereby moving the tubular sleeve 205 proximally with respect to the stop 215, such that the stop 215 is no longer within the tubular sleeve and is clear of the distal opening 230. As described above, movement of the inner member 220 in this way serves to move the band 225 into engagement with the free-floating ring 210 and to move the free-floating ring into engagement with the proximal end 105 of the vascular device 100. The proximal portion 115 of the vascular device 100 may thus be deployed from the distal opening 230 of the tubular sleeve 205 and is free to fully self-expand against the vessel wall. Block 660.

Finally, after the vascular device is in position at the target site and is fully deployed from the tubular sleeve of the delivery device and/or the delivery sheath, the delivery device may be withdrawn from the body lumen. Block 665. In cases where a delivery sheath is used, the operator may also withdraw the delivery sheath and/or the guidewire from the body lumen, leaving only the vascular device in place at the target site.

FIGS. 10-11, discussed above, present flowcharts of a method for deploying a vascular device within a body lumen according to example embodiments of the delivery device. Dashed lines and boxes indicate optional steps of the method. Additionally, although the steps are presented in a particular order in FIGS. 10-11, some of the steps may be performed in an order other than what is presented in the figures or may occur substantially simultaneously with other steps according to the particular vascular device being used, the intravascular procedure being conducted, the configuration of the delivery device, the operator's choice of other delivery tools, instruments, and accessories with which the delivery device is used, and other user preferences.

According to the embodiments described above and illustrated in the accompanying figures, embodiments of a delivery device are thus provided that are configured to maintain a proximal end of a vascular device within the tubular sleeve without physically wedging the proximal end against the walls of the tubular sleeve, as is the case in certain conventional delivery devices. As a result, a lower applied force is required to deploy the vascular device from the tubular sleeve, minimizing the risk of impairing the vascular device or disturbing the positioning of the vascular device at the target site as the vascular device is deployed. In addition, the embodiments described herein allow for the recapture and repositioning of the vascular device within a delivery sheath prior to the full deployment of the proximal end of the vascular device from the tubular sleeve within which the proximal end is retained, providing greater flexibility and ease of use to the operator.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A device for delivering a vascular device within a body lumen, the delivery device comprising:
    a tubular sleeve defining a distal opening;
    an inner member at least partially disposed within the tubular sleeve and configured to move axially therein, wherein the inner member defines a proximal end and a distal end, and wherein the inner member comprises a stop fixedly disposed proximate the distal end, a first band of increased thickness fixedly disposed at a predetermined distance from the stop, such that the first band is proximally disposed with respect to the stop, and a second band of increased thickness fixedly disposed at a predetermined distance between the first band and the stop; and
    a free-floating ring slideably received on the inner member and within the tubular sleeve and configured to slide along the inner member between the first band and the second band,
    wherein the tubular sleeve and the inner member are configured to receive a proximal portion of a vascular device therebetween such that, when the stop is disposed within the tubular sleeve and within the proximal portion of the vascular device, the proximal end of the vascular device is maintained within the tubular sleeve, and
    wherein, when the inner member is moved relative to the tubular sleeve, the free-floating ring is configured to cooperate with the first band to push the proximal end of the vascular device through the distal opening of the tubular sleeve to deploy the vascular device.

2. The delivery device of claim 1, wherein the predetermined distance between the first band and the stop is greater than an axial length of the tubular sleeve.

3. The delivery device of claim 1, wherein a distal portion of the vascular device extends distally from the distal opening of the tubular sleeve.

4. The delivery device of claim 1, wherein the free-floating ring defines a circular void via which the free-floating ring is slideable along the inner member, wherein the void defines a void diameter that is smaller than an outer diameter of the first band and the second band, such that the free-floating ring is maintained on the inner member between the first band and the second band.

5. The delivery device of claim 1, wherein the free-floating ring defines a proximal surface and a distal surface, wherein the proximal surface is configured to abut a corresponding surface of the first band so as to cause the free-floating ring to move with the first band in response to relative distal movement of the inner member with respect to the tubular sleeve, and wherein the distal surface of the free-floating ring is configured to engage the proximal end of the vascular device to push the vascular device out of the distal opening of the tubular sleeve in response to continued relative distal movement of the inner member with respect to the tubular sleeve.

6. The delivery device of claim 1, wherein the stop defines an outer diameter that is smaller than an inner diameter of the tubular sleeve, such that, when the stop is disposed within the tubular sleeve, an annular clearance is defined between the stop and an inner surface of the tubular sleeve.

7. The delivery device of claim 6, wherein the tubular sleeve is configured to receive a proximal portion of a vascular device comprising a section of increased thickness, wherein a wall thickness of the vascular device at the section of increased thickness is greater than the annular clearance defined by the tubular sleeve, such that the proximal portion of the vascular device is retained within the tubular sleeve when the stop is disposed within the tubular sleeve.

8. The delivery device of claim 1, wherein at least one of the stop or the first band is integral to the inner member.

9. The delivery device of claim 1, wherein the inner member defines a lumen configured to receive a guidewire therethrough.

10. The delivery device of claim 1 further comprising an intermediate tubular member, wherein a proximal end of the tubular sleeve is configured to engage a distal end of the intermediate tubular member.

11. The delivery device of claim 10, wherein the tubular sleeve comprises an adapter configured to couple the intermediate tubular member and the tubular sleeve together, wherein the adapter comprises a distal portion defining a first outer diameter, a proximal portion defining a second outer diameter, and a transition portion therebetween, wherein the first outer diameter corresponds to an inner diameter of the tubular sleeve and the second outer diameter corresponds to an inner diameter of the intermediate tubular member.

12. The delivery device of claim 1, wherein the delivery device is configured to be axially moveable through a delivery sheath.

13. The delivery device of claim 1, wherein the second band of increased thickness is configured to engage a distal surface of the free-floating ring when the inner member is moved in a proximal direction with respect to the tubular sleeve.

14. A system for delivering a vascular device within a body lumen, the system comprising:
- a delivery device comprising:
  - a tubular sleeve defining a distal opening;
  - an inner member at least partially disposed within the tubular sleeve and configured to move axially therein, wherein the inner member defines a proximal end and a distal end, and wherein the inner member comprises a stop fixedly disposed proximate the distal end, a first band of increased thickness fixedly disposed at a predetermined distance from the stop, such that the first band is proximally disposed with respect to the stop, and a second band of increased thickness fixedly disposed at a predetermined distance between the first band and the stop; and
  - a free-floating ring slideably received on the inner member and within the tubular sleeve and configured to slide along the inner member between the first band and the second band;
- a delivery sheath defining a lumen configured to receive the delivery device therethrough;
- a device loader configured to slideably extend about a portion of the delivery device so as to at least partially constrain a distal portion of a vascular device to allow the vascular device to be received within the lumen of the delivery sheath,
- wherein the delivery sheath is configured to be positioned within the body lumen proximate a target site,
- wherein the tubular sleeve and the inner member of the delivery device are configured to receive a proximal portion of the vascular device therebetween such that, when the stop is disposed within the tubular sleeve and within the proximal portion of the vascular device, the proximal end of the vascular device is maintained within the tubular sleeve,
- wherein the delivery device and the received vascular device are configured to be moved distally through the lumen of the delivery sheath toward the target site, and
- wherein, when the inner member is moved relative to the tubular sleeve, the free-floating ring is configured to cooperate with the first band to push the proximal end of the vascular device through the distal opening of the tubular sleeve to deploy the vascular device.

* * * * *